(12) United States Patent
Bruszewski et al.

(10) Patent No.: US 8,506,622 B2
(45) Date of Patent: Aug. 13, 2013

(54) MOBILE EXTERNAL COUPLING FOR BRANCH VESSEL CONNECTION

(75) Inventors: Walter Bruszewski, Guerneville, CA (US); Kevin Boyle, Renmore (IE); Masoumeh Mafi, Mountain View, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 114 days.

(21) Appl. No.: 12/425,628

(22) Filed: Apr. 17, 2009

(65) Prior Publication Data
US 2010/0268319 A1 Oct. 21, 2010

(51) Int. Cl.
*A61F 2/06* (2006.01)

(52) U.S. Cl.
USPC ........ 623/1.35; 623/1.13; 623/1.16; 623/1.22

(58) Field of Classification Search
USPC .............................. 623/1.12, 1.16, 1.22, 1.35
See application file for complete search history.

(56) References Cited

U.S. PATENT DOCUMENTS

| | | | |
|---|---|---|---|
| 3,692,618 A | 9/1972 | Dorschner et al. | |
| 3,802,817 A | 4/1974 | Matsuki et al. | |
| 4,340,563 A | 7/1982 | Appel et al. | |
| 5,387,235 A | 2/1995 | Chuter | |
| 5,456,713 A | 10/1995 | Chuter | |
| 5,693,084 A | 12/1997 | Chuter | |
| 5,709,713 A | 1/1998 | Evans et al. | |
| 5,720,776 A | 2/1998 | Chuter et al. | |
| 5,800,514 A | 9/1998 | Nunez et al. | |
| 5,984,955 A | 11/1999 | Wisselink | |
| 6,187,035 B1 | 2/2001 | Jang | |
| 6,248,067 B1 | 6/2001 | Beitz et al. | |
| 6,319,277 B1 * | 11/2001 | Rudnick et al. | 623/1.13 |
| 6,428,565 B1 | 8/2002 | Wisselink | |
| 6,465,073 B1 | 10/2002 | Morman et al. | |
| 6,565,214 B1 | 5/2003 | Shinobu | |
| 6,565,597 B1 | 5/2003 | Fearnot et al. | |
| 6,616,675 B1 | 9/2003 | Evard et al. | |
| 6,645,242 B1 | 11/2003 | Quinn | |
| 6,689,162 B1 | 2/2004 | Thompson | |
| 6,994,724 B2 | 2/2006 | Schmitt | |
| 7,189,257 B2 * | 3/2007 | Schmitt et al. | 623/1.51 |
| 7,264,632 B2 | 9/2007 | Wright et al. | |
| 7,645,298 B2 * | 1/2010 | Hartley et al. | 623/1.35 |
| 7,842,081 B2 * | 11/2010 | Yadin | 623/1.35 |
| 8,241,349 B2 * | 8/2012 | Davidson et al. | 623/1.35 |

(Continued)

FOREIGN PATENT DOCUMENTS

| | | |
|---|---|---|
| EP | 0556749 | 2/1993 |
| EP | 1201212 | 5/2002 |

(Continued)

*Primary Examiner* — Thomas J Sweet
*Assistant Examiner* — Seema Mathew

(57) ABSTRACT

An endovascular prosthesis includes a tubular body and a flexible springy mobile external coupling. The tubular body includes a graft material and stents coupled thereto with a forms a lumen therethrough. The mobile external coupling extends outwardly from the tubular body. The mobile external coupling includes a graft material and is generally frustoconically shaped. The mobile external coupling includes a base coupled to the tubular body, a top spaced from the tubular body, and a coupling lumen disposed between the base and the top, wherein the coupling lumen is in flow communication with the body lumen. A helically shaped stent may be coupled to the coupling graft material to make it flexible and springy.

25 Claims, 6 Drawing Sheets

(56) References Cited

U.S. PATENT DOCUMENTS

| | | |
|---|---|---|
| 2001/0003161 A1 | 6/2001 | Vardi et al. |
| 2003/0130720 A1 | 7/2003 | DePalma et al. |
| 2003/0195609 A1 | 10/2003 | Berenstein et al. |
| 2003/0199967 A1 | 10/2003 | Hartley et al. |
| 2005/0063578 A1 | 3/2005 | Zhang et al. |
| 2005/0102021 A1* | 5/2005 | Osborne ............... 623/1.13 |
| 2005/0143806 A1 | 6/2005 | Phillips |
| 2005/0171597 A1* | 8/2005 | Boatman et al. ........... 623/1.22 |
| 2005/0222668 A1 | 10/2005 | Schaeffer et al. |
| 2005/0288775 A1 | 12/2005 | Dong |
| 2006/0155362 A1 | 7/2006 | Israel |
| 2006/0229561 A1 | 10/2006 | Huszar |
| 2006/0247760 A1 | 11/2006 | Ganesan et al. |
| 2006/0247761 A1* | 11/2006 | Greenberg et al. ........... 623/1.16 |
| 2006/0276883 A1 | 12/2006 | Greenberg et al. |
| 2007/0118208 A1 | 5/2007 | Kerr |
| 2007/0135904 A1 | 6/2007 | Eidenschink et al. |
| 2007/0208419 A1 | 9/2007 | Meyer et al. |
| 2007/0244542 A1* | 10/2007 | Greenan et al. ............... 623/1.13 |
| 2008/0114442 A1 | 5/2008 | Mitchell et al. |
| 2008/0262590 A1 | 10/2008 | Murray |
| 2009/0012596 A1* | 1/2009 | Kocur et al. ................ 623/1.11 |
| 2009/0030502 A1* | 1/2009 | Sun et al. ................... 623/1.16 |
| 2009/0048663 A1* | 2/2009 | Greenberg .................. 623/1.35 |
| 2009/0093873 A1* | 4/2009 | Navia ........................ 623/1.23 |
| 2009/0163993 A1* | 6/2009 | Chalekian et al. ............ 623/1.15 |
| 2009/0164001 A1* | 6/2009 | Biggs et al. ................. 623/1.35 |
| 2009/0248315 A1 | 10/2009 | Pardo et al. |
| 2009/0264991 A1* | 10/2009 | Paul et al. .................... 623/1.35 |
| 2009/0276027 A1 | 11/2009 | Glynn |
| 2010/0057186 A1* | 3/2010 | West et al. .................... 623/1.13 |
| 2010/0063576 A1* | 3/2010 | Schaeffer et al. ............ 623/1.13 |
| 2010/0114294 A1 | 5/2010 | Rasmussen et al. |
| 2010/0121429 A1* | 5/2010 | Greenan et al. ............... 623/1.15 |
| 2010/0137573 A1* | 6/2010 | Huang ........................ 536/25.3 |
| 2011/0066220 A1* | 3/2011 | Laguna ........................ 623/1.2 |
| 2011/0166644 A1* | 7/2011 | Keeble et al. ................. 623/1.24 |
| 2012/0065652 A1* | 3/2012 | Cully et al. ................... 606/153 |
| 2012/0197383 A1* | 8/2012 | Ivancev et al. ............... 623/1.13 |
| 2013/0079870 A1* | 3/2013 | Roeder et al. ................. 623/1.35 |

FOREIGN PATENT DOCUMENTS

| | | |
|---|---|---|
| EP | 1386624 | 2/2006 |
| EP | 1847236 | 10/2007 |
| EP | 1847237 | 10/2007 |
| WO | WO93/16669 | 9/1993 |
| WO | WO97/25002 | 7/1997 |
| WO | WO02/067815 | 9/2002 |
| WO | WO2005/032340 | 4/2005 |
| WO | WO2005/034809 | 4/2005 |
| WO | WO2005/034810 | 4/2005 |
| WO | WO2005/037160 | 4/2005 |
| WO | WO2006/013501 | 2/2006 |
| WO | WO2006/113501 | 10/2006 |
| WO | WO2007/055768 | 5/2007 |
| WO | WO2010/024849 | 3/2010 |
| WO | WO2010/024879 | 3/2010 |

\* cited by examiner

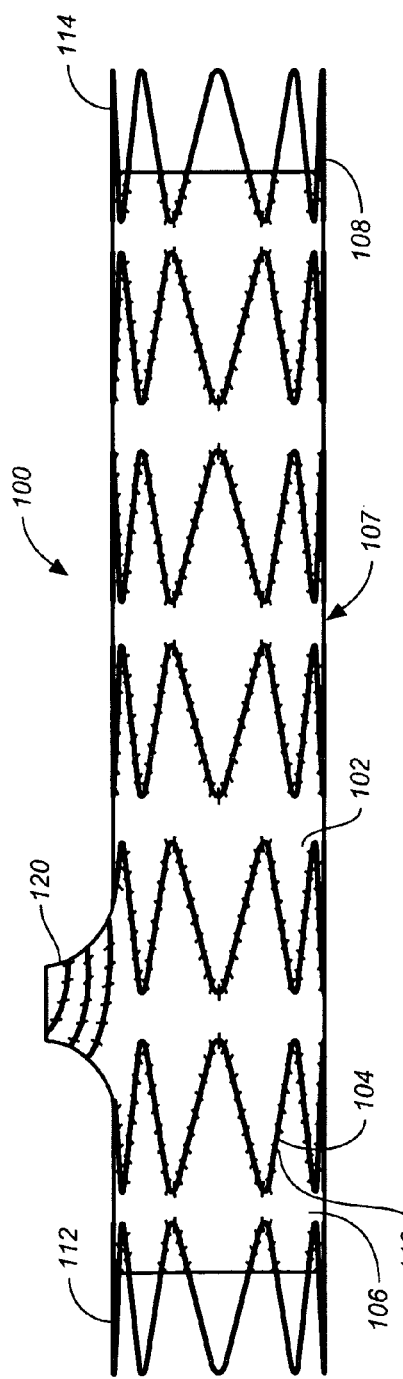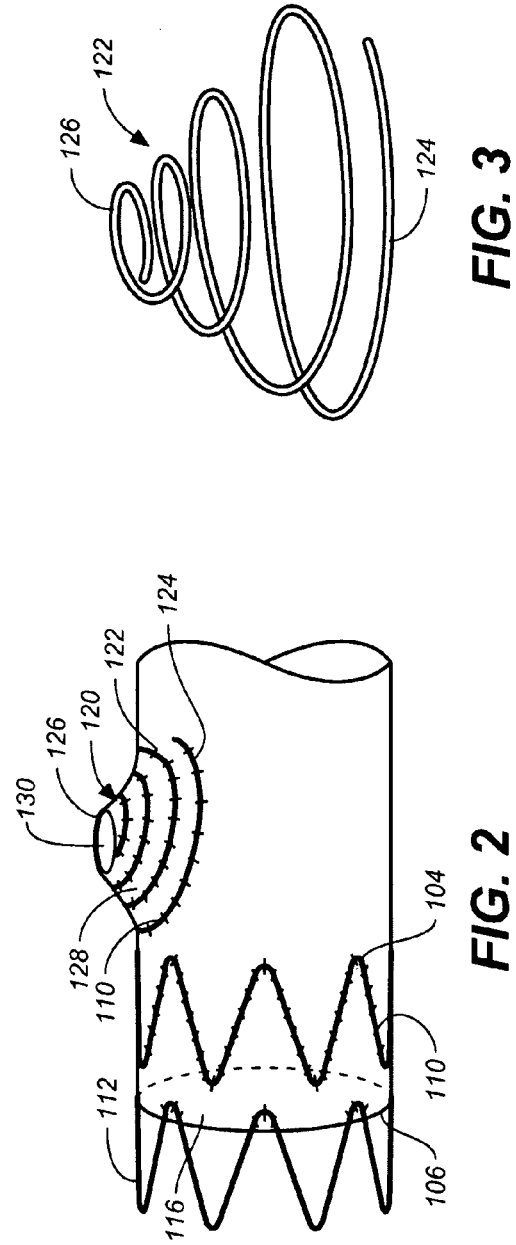

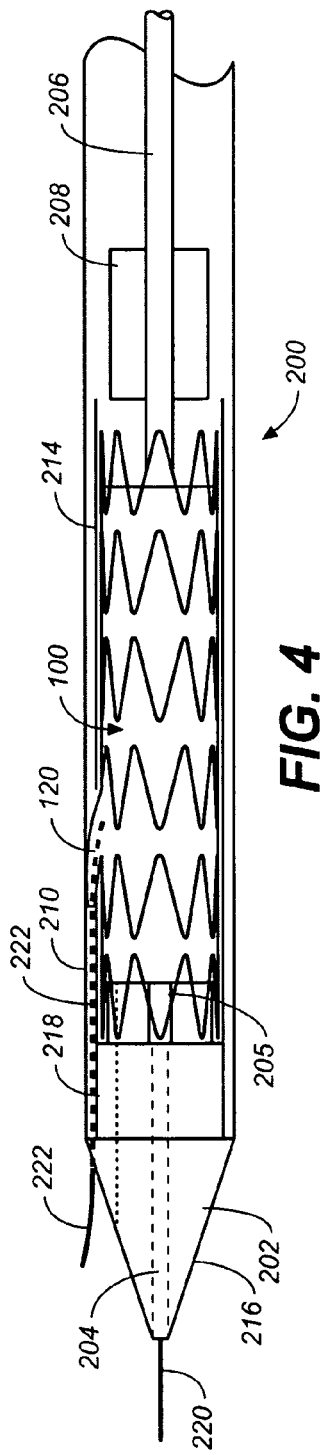
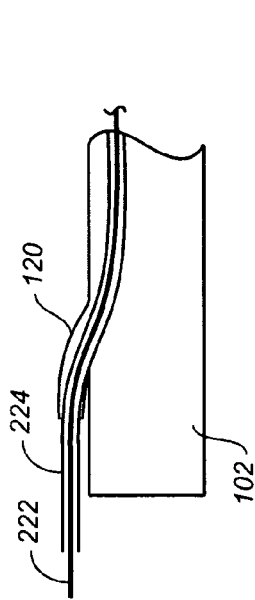
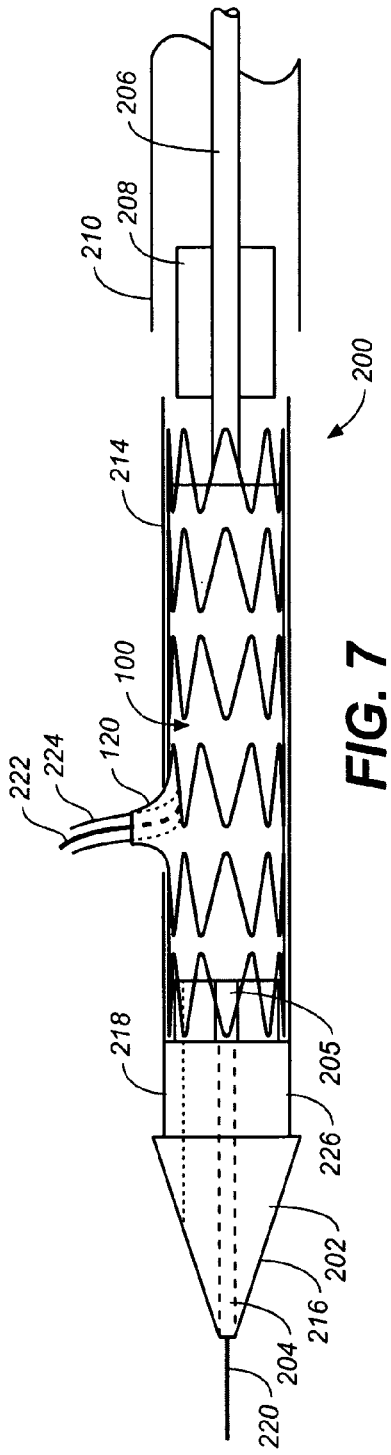

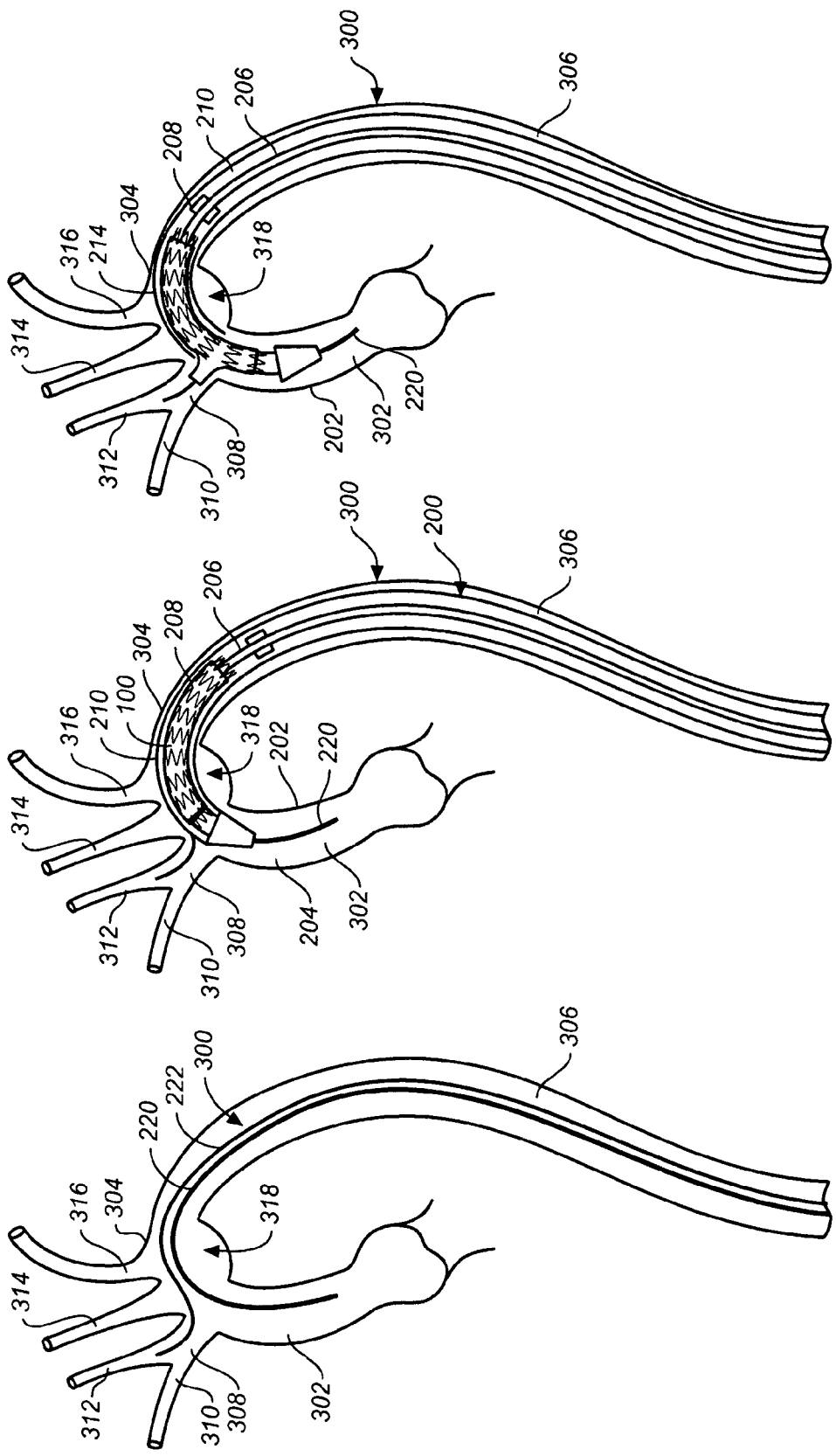

MOBILE EXTERNAL COUPLING FOR BRANCH VESSEL CONNECTION

FIELD OF THE INVENTION

This invention relates generally to endoluminal medical devices and procedures, and more particularly to an endoluminal prosthesis or graft having a mobile external coupling for connecting a main graft to a branch vessel graft.

BACKGROUND

Aneurysms and/or dissections may occur in blood vessels, and most typically occur in the aorta and peripheral arteries. Depending on the region of the aorta involved, the aneurysm may extend into areas having vessel bifurcations or segments of the aorta from which smaller "branch" arteries extend. Various types of aortic aneurysms may be classified on the basis of the region of aneurysmal involvement. For example, thoracic aortic aneurysms include aneurysms present in the ascending thoracic aorta, the aortic arch, and branch arteries that emanate therefrom, such as subclavian arteries, and also include aneurysms present in the descending thoracic aorta and branch arteries that emanate therefrom, such as thoracic intercostal arteries and/or the suprarenal abdominal aorta and branch arteries that emanate therefrom, such as renal, superior mesenteric, celiac and/or intercostal arteries. Lastly, abdominal aortic aneurysms include aneurysms present in the aorta below the diaphragm, e.g., pararenal aorta and the branch arteries that emanate therefrom, such as the renal arteries.

The thoracic aorta has numerous arterial branches. The arch of the aorta has three major branches extending therefrom, all of which arise from the convex upper surface of the arch and ascend through the superior thoracic aperture to the root of the neck. The brachiocephalic artery originates anterior to the trachea. The brachiocephalic artery divides into two branches, the right subclavian artery (which supplies blood to the right arm) and the right common carotid artery (which supplies blood to the right side of the head and neck). The left common carotid artery arises from the arch of the aorta just to the left of the origin of the brachiocephalic artery. The left common carotid artery supplies blood to the left side of the head and neck. The third branch arising from the aortic arch, the left subclavian artery, originates behind and just to the left of the origin of the left common carotid artery and supplies blood to the left arm.

For patients with thoracic aneurysms of the aortic arch, surgery to replace the aorta may be performed where the aorta is replaced with a fabric substitute in an operation that uses a heart-lung machine. In such a case, the aneurysmal portion of the aorta is removed or opened and a substitute lumen is sewn across the aneurysmal portion. Such surgery is highly invasive, requires an extended recovery period and, therefore, cannot be performed on individuals in fragile health or with other contraindicative factors.

Alternatively, the aneurysmal region of the aorta can be bypassed by use of a tubular exclusion device, e.g., by a stent-graft placed inside the vessel spanning the aneurysmal portion of the vessel, to seal off the aneurysmal portion from further exposure to blood flowing through the aorta. A stent-graft can be implanted without a chest incision, using specialized catheters that are introduced through arteries, usually through incisions in the groin region of the patient. The use of stent-grafts to internally bypass, within the aorta or flow lumen, the aneurysmal site, is also not without issues. In particular, where a stent-graft is used in a thoracic location, care must be taken so that critical branch arteries are not covered or occluded by the stent-graft yet the stent-graft must seal against the aorta wall and provide a flow conduit for blood to flow past the aneurysmal site. Where the aneurysm is located immediately adjacent to the branch arteries, there is a need to deploy the stent-graft in a location which partially or fully extends across the location of the origin of the branch arteries from the aorta to ensure sealing of the stent-graft to the artery wall.

To accommodate side branches, main vessel stent-grafts having a fenestration or opening in a side wall thereof may be utilized. The main vessel stent graft is positioned to align the fenestration with the ostium of the branch vessel after deployment. In use, a proximal end of the stent-graft, having one or more side openings, is prepositioned and securely anchored in place so that the fenestrations or openings are oriented and deployed in the main vessel to avoid blocking or restricting blood flow into the side branches. Fenestrations by themselves do not form or include discrete conduit(s) through which blood can be channeled into the adjacent side branch artery. As a result, blood leakage is prone to occur into the space between the outer surface of the aortic graft and the surrounding aortic wall between the edges of the graft surrounding the fenestrations and the adjacent vessel wall. Similar blood leakage can result from post-implantation migration or movement of the stent-graft causing misalignment of the fenestration(s) and the branch artery(ies), which may also result in impaired flow into the branch artery(ies).

In some cases, the main vessel stent graft is supplemented by another stent-graft, often referred to as a branch stent-graft. The branch graft is deployed through the fenestration into the branch vessel to provide a conduit for blood flow into the branch vessel. The branch stent-graft is preferably sealingly connected to the main graft in situ to prevent undesired leakage. This connection between the branch graft and main graft may be difficult to create effectively in situ and is a site for potential leakage.

In some instances, branch graft extensions (stent-grafts) are incorporated into the main stent-graft. Such branch graft extensions are folded or collapsed against the main stent-graft for delivery and require complicated procedures, requiring multiple sleeves and guidewires, to direct the branch extension into the branch vessel and subsequently expand. Further, in some instances, such branch stent-grafts tend to return to their folded or collapsed configuration, and thus do not provide an unobstructed flow path to the branch vessel.

Thus, there remains a need in the art for improvements for directing flow from a main vessel, such as the aorta, into corresponding branch vessels, such as branch vessels of the aortic arch.

SUMMARY OF THE INVENTION

An embodiment of an endovascular prosthesis includes a tubular body and a mobile external coupling. The tubular body includes a graft material and stents coupled thereto, a forms a lumen therethrough. The mobile external coupling extends outwardly from the tubular body. The mobile external coupling includes a graft material and is generally frustoconically shaped. The mobile external coupling includes a base coupled to the tubular body, a top spaced from the tubular body, and a coupling lumen disposed between the base and the top, wherein the coupling lumen is in flow communication with the body lumen. A helically shaped stent may be coupled to the coupling graft material. The configuration of the mobile external coupling provides flexibility for coupling the prosthesis to a branch vessel prosthesis.

In a method for delivering and deploying the endovascular prosthesis a main prosthesis is delivered in a compressed configuration to a target location in a main vessel such that the mobile external coupling is generally aligned with a branch vessel. A sleeve is retracted to expose the mobile external coupling. Minor adjustments to the location of the mobile external coupling to better align it with the branch vessel may be necessary. The tubular body is deployed such that it expands from the compressed configuration to an expanded configuration. A branch vessel prosthesis may be delivered in a compressed configuration to the branch vessel. The branch vessel prosthesis may be deployed such that the branch vessel prosthesis radially expands to an expanded configuration and an outside surface of a portion of the branch vessel prosthesis is in contact with an inner surface of a portion of the mobile external coupling.

BRIEF DESCRIPTION OF DRAWINGS

The foregoing and other features and advantages of embodiments according to the invention will be apparent from the following description as illustrated in the accompanying drawings. The accompanying drawings, which are incorporated herein and form a part of the specification, further serve to explain the principles of the embodiments and to enable a person skilled in the pertinent art to make and use the described embodiments herein. The drawings are not to scale.

FIG. 1 is a schematic side view of an endoluminal stent-graft according to an embodiment hereof.

FIG. 2 is a schematic close up illustration of a portion of the stent-graft of FIG. 1.

FIG. 3 is a schematic illustration of a stent portion of the mobile external coupling of the stent-graft of FIG. 1.

FIG. 4 is a schematic illustration of a stent-graft delivery device.

FIG. 5 is a schematic perspective view of the tip of the stent-graft delivery device of FIG. 4.

FIG. 6 is a schematic illustration of a portion of the stent-graft and a portion of the stent-graft delivery device.

FIGS. 7 and 8 are schematic illustrations of the stent-graft delivery device of FIG. 4 as the sheath is retracted.

FIGS. 9-14 are schematic illustrations of progressive steps of a method for delivering and deploying the stent-graft of FIG. 1 and a branch stent-graft to a target location.

DETAILED DESCRIPTION

Figure 8:
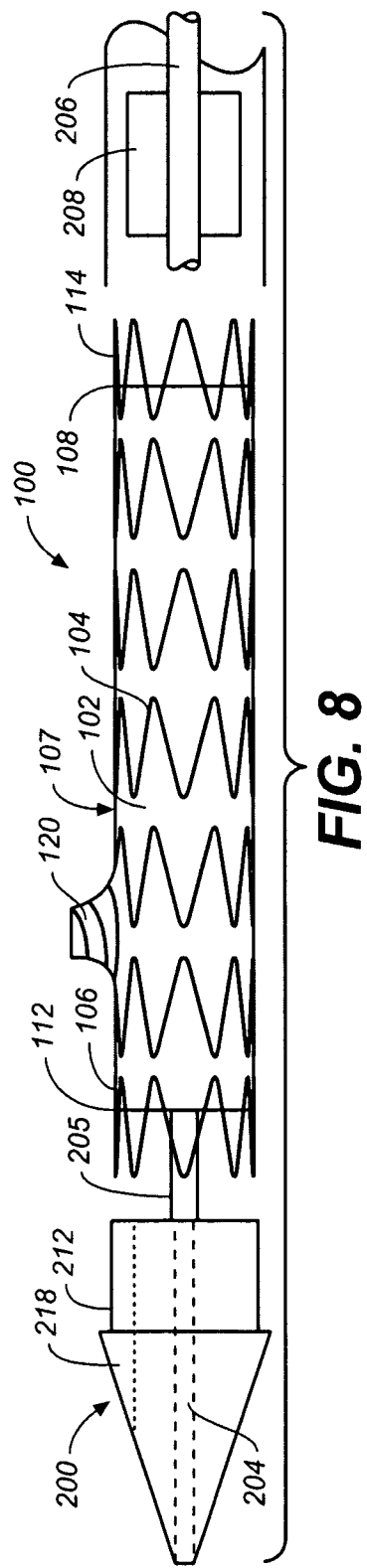

Specific embodiments are now described with reference to the figures, wherein like reference numbers indicate identical or functionally similar elements. Unless otherwise indicated, for the delivery system the terms "distal" and "proximal" are used in the following description with respect to a position or direction relative to the treating clinician. "Distal" and "distally" are positions distant from or in a direction away from the clinician, and "proximal" and "proximally" are positions near or in a direction toward the clinician. For the stent graft device proximal is the portion nearer the heart by way of blood flow path while distal is the portion of the stent graft further from the heart by way of blood flow path.

With reference to FIGS. 1-3, a stent-graft 100 is configured for placement in a vessel such as the aorta. Stent-graft 100 includes graft material 102 coupled to stents 104. Graft material 102 may be coupled to stents 104 using stitching 110 or other means known to those of skill in the art. In the embodiment shown in FIGS. 1-3 stents 104 are coupled to an outside surface of graft material 102. However, stents 104 may alternatively be coupled to an inside surface of graft material 102. Graft material 102 may be any suitable graft material, for example and not limited to, woven polyester, DACRON material, expanded polytetrafluoroethylene, polyurethane, silicone, or other suitable materials. Stents 104 may be any conventional stent material or configuration. As shown, stents 104 are preferably made from a shape memory material, such as thermally treated stainless steel or nickel-titanium alloy (nitinol), and are formed into a zig-zag configuration. Stent-graft 100 includes a proximal end 106, a distal end 108, and a body 107 therebetween. Proximal stent 112 and distal stent 114 may extend outside of the graft material 102, as shown, and may also be generally described as anchor stents or crown stents in the art. Body 107 has a lumen 116 disposed therethrough. Stent-graft 100 further includes a mobile external coupling 120, described in detail below. Except for the mobile external coupling 120, stent graft-100 may be similar to the Medtronic, Inc.'s VALIANT® thoracic stent-graft, or other known stent-grafts.

Mobile external coupling 120 is disposed on an outside surface of stent-graft 100 at an opening in graft material 102. Mobile external coupling 120 is generally frustoconically shaped. Mobile external coupling 120 includes graft material 128 coupled to a helical stent 122. Graft material 128 is preferably the same type of graft material as graft material 102 of the body 107 and is preferably a continuation of graft material 102, although graft material 128 can be a separate piece of graft material attached to graft material 102. Mobile external coupling 120 and stent 122 include a base 124 and a top 126. Although mobile external coupling 120 is described as generally frustoconical in shape, base 124 is preferably generally elliptical rather than circular. Base 124 may have, for example and not by way of limitation, a long axis of approximately 20-30 mm and a short axis of approximately 15-20 mm. Further, the height of mobile external coupling 120 may be approximately 10-15 mm. Further, the diameter of the top 126 of mobile external coupling may be approximately 6-9 mm if it is to be used at the junction of the aorta and left common carotid artery or the junction of the aorta and left subclavian artery. If the mobile external coupling 120 is to be used at the junction of the aorta and the brachiocephalic artery, the diameter of the top 126 may be approximately 8-12 mm.

Stent 122 of mobile external coupling 120 is generally helical and configured to create frustoconically shaped outline such that bottom 124 has a larger diameter than top 124, as shown schematically in FIG. 3. Stent 122 is coupled to graft material 128 using stitches (e.g., 110) or other similar coupling means. Stent 122 is preferably made from shape memory material such a nitinol. Stent 122 may be made from the same material as main body stents 104 or may be made from different material. For example, stents 104 may be balloon expandable and stent 122 may be self-expanding. Preferably, stents 104 and stent 122 are made from shape memory materials such as nitinol and are self-expanding.

Mobile external coupling 120 allows for significant flexibility in aligning stent-graft 100 with a branch vessel because the top of the mobile external coupling 120 can move. This mobility is due to the shape of mobile external coupling 120 and can be further improved by utilizing some excess graft material 128 when forming mobile external coupling 120. Thus, if stent-graft 100 is not perfectly aligned with a branch vessel, the top 126 of mobile external coupling 120 can be moved or shifted such that mobile external coupling 120 will extend into the branch vessel. Further, due to the force stored in the shape memory helical stent 122, mobile external coupling 120 pops out from body 107 of stent-graft 100 when released from a sleeve during delivery to a target site. This prevents bunching or collapse of the mobile external coupling 120 when released from the delivery system.

FIGS. 4-8 show an example of a delivery system that can be used to delivery stent-graft 100 to the target location within a vessel. FIG. 4 is a schematic partial cross-sectional view of a stent-graft delivery system 200 with stent-graft 100 disposed therein. Stent-graft delivery system 200 includes a tapered tip 202 that is flexible and able to provide trackability in tight and tortuous vessels. Other tip shapes such as bullet-shaped tips could also be used. The tip 202 includes a lumen 204 disposed therethrough for accommodating a first guidewire 220.

The tapered tip 202 includes a tapered outer surface 216 that gradually decreases in diameter in a distal direction. More particularly, tapered outer surface 216 has a first diameter at a proximal end and gradually decreases in diameter distally, i.e., in the direction away from the operator. Tapered outer surface 216 further includes a groove 218, as best seen in FIG. 5, for accommodating a second guidewire 222. A shoulder 212 reduces the diameter of a proximal portion of tip 202 to provide a sleeve landing surface 226. Shoulder 212 is generally annular and perpendicular to a longitudinal axis of stent-graft delivery system 200.

A first or outer sleeve 210 of stent-graft delivery system 200 extends over the outer cylindrical surface of sleeve landing surface 220 and abuts against shoulder 212 when the stent-graft delivery system 200 is in a pre-deployment configuration, as shown in FIG. 4. A second or inner sleeve 214 is disposed within outer sleeve 210. Inner sleeve 214 includes an opening through which mobile external coupling 120 extends, as described in more detail below.

Stent-graft delivery system 200 also includes an inner tube 205 that is coupled to a tip lumen 204 such that first guidewire 220 may extend the length of delivery system 200. Delivery system 200 may also include an outer tube 206 surrounding inner tube 205. A stop 208 is located at a distal end of stent-graft 100 when stent-graft 100 is loaded onto the delivery system 200. Stop 208 prevents longitudinal movement of stent-graft 100 as outer and inner sleeves 210, 214 are retracted or otherwise removed to release stent-graft 100. Stent-graft 100 is disposed within outer and inner sleeves 210, 214 in a compressed or delivery configuration wherein the diameter of stent-graft 100 is reduced such that it can be inserted through the vasculature.

Second guidewire 222 extends through stent-graft delivery system 200, through lumen 116 of stent-graft 100, through lumen 130 of mobile external coupling 120, between inner sleeve 214 and outer sleeve 210, and out a distal end of outer sleeve 210 through groove 218 of tip 202. A tube 224 may be provided to guide second guidewire 222 along this path and tube 224 may extend proximally to the proximal portion of delivery system 200. In the delivery or compressed configuration, mobile external coupling 120 may be folded proximally as shown schematically in FIGS. 4 and 6.

Outer sleeve 210 is a hollow tube and defines a lumen therein within which outer tube 206, inner tube 204, inner sleeve 214, and stent-graft 100 are disposed in the delivery configuration. Outer sleeve 210 is moved proximally, i.e. retracted, relative to outer tube 206 to release or deploy mobile external coupling 120. FIG. 7 shows outer sleeve 210 retracted and mobile external coupling 120 extended (deployed). After outer sleeve 210 is retracted, inner sleeve 214 is removed by, for example, a pull wire or other method known to those skilled in the art. A conventionally retracted inner sleeve 214 is not desirable because it would interfere with mobile external coupling 120. However, a pull string (not shown) to create a longitudinal slit to split inner sleeve 214 prior to retracting it may be used. Alternatively, a weakened (frangible) area (line) in inner sleeve 214 distal to mobile external coupling 120 may be utilized such that retracting inner sleeve 214 would cause the weakened area to split around mobile external coupling 120. Other means to accommodate mobile external coupling 120 when retracting inner sleeve 214 may be utilized, as would be apparent to those skilled in the art. Retracting inner sleeve 214 allows stent-graft 100 to deploy from its compressed configuration to its deployed or expanded configuration, as shown schematically in FIG. 8.

The stent-graft delivery system 200 described herein is only an example of a delivery system that can be used to delivery and deploy stent-graft 100 and many other delivery systems known to those skilled in the art could be utilized. For example, stent-graft 100 could be mounted onto a balloon to be expanded when at the target site. Other stent-graft-delivery systems, for example and not by way of limitation, the delivery systems described in U.S. Published Patent Application Publication Nos. 2008/0114442 and 2008/0262590 and U.S. Pat. No. 7,264,632, each of which is incorporated herein by reference in its entirety, may be utilized to deliver and deploy stent graft 100.

FIGS. 9-14 schematically show a method of delivering stent-graft 100 to a target site in a main vessel and a method of delivering a branch stent-graft to branch vessel. In the example described herein, the stent-graft 100 is delivered and deployed into the aorta 300. Portions of the aorta 300 include the ascending aorta 302, the aortic arch 304, and the descending aorta 306. Branching from the aortic arch are the brachiocephalic trunk 308, the left common carotid artery 314, and the left subclavian artery 316. The brachiocephalic trunk branches into the right subclavian artery 310 and the right common carotid artery 312. An aneurysm 318 in the area of the aortic arch 304 can be difficult to bypass or exclude with a stent-graft because blood flow to the branch arteries must be maintained.

In the embodiment shown in FIGS. 9-14, the aneurysm is sufficiently close to brachiocephalic trunk 308 that the stent-graft must extend between the brachiocephalic trunk 308 and the heart. In such a case and with a stent-graft 100 with only a single mobile external coupling 120, the mobile external coupling 120 is designed so as to be deployed into the brachiocephalic trunk 308 to perfuse the brachiocephalic trunk 308. Prior to the procedure for inserting stent-graft 100, a by-pass procedure installing bypass grafts or vessels (not shown) is performed to connect the right common carotid artery 312 to the left common carotid artery 314 and the left common carotid artery to the left subclavian artery 316. Such a procedure may be performed one to two weeks prior to insertion of the stent-graft, and presents significantly less complications and risk than a surgical solution to repair an aneurysm 318 in the aortic arch. In this manner, maintaining perfusion to the brachiocephalic trunk 308, and hence the right common carotid artery 312, maintains perfusion to the left common carotid artery 314 and the left subclavian artery 314. Thus, the openings (or ostia) to these branch vessels directly from the aortic arch may be blocked by stent-graft 100. In the alternative, multiple mobile external couplings 120 may be provided in stent-graft 100. Further, if the aneurysm only affects the left common carotid artery 314 and the left subclavian artery 316, only one by-pass between the left common carotid artery 314 and the left subclavian artery needs to be performed, and then a stent-graft with a single mobile external coupling 120 can be utilized to perfuse the left common carotid artery 314. Alternatively, in such a situation, a stent-graft with two mobile external couplings may be provided, one for each of the branch vessels noted. Accordingly, while the embodiment of stent-graft 100 in the method described below includes a single mobile external coupling 120 and the mobile external coupling is deployed in the brachiocephalic trunk 308, those skilled in the art would recognize that multiple mobile external coupling can be used and the mobile external coupling(s) may be deployed in other branch arteries.

FIG. 9 shows the first guidewire 220 advanced from the descending aorta 306, through the aortic arch 304, and into the ascending aorta 302 and second guidewire 222 advanced from the descending aorta 306, through the aortic arch 304, and into brachiocephalic trunk 308. Guidewires 200, 222 are typically inserted into the femoral artery and routed up through the abdominal aorta, and into the thoracic aorta, as is known in the art.

FIG. 10 shows stent-graft delivery system 200, with stent-graft 100 compressed therein, advanced over guidewires 220, 222 to the target location in the aortic arch 304. The location of the stent-graft delivery system 200 and/or the stent-graft 100 may be verified radiographically and delivery system 200 and/or stent-graft 100 may include radiopaque markers as known in the art.

After stent-graft delivery system 200 is in the proper location with the mobile external coupling 120 of the stent graft 100 approximately aligned with the opening into the branch vessel, outer sleeve 210 is retracted proximally to release mobile external coupling 120, as shown in FIG. 11. Mobile external coupling 120 provides a positive outward force due to helical stent 122 that reduces the possibility of the mobile external coupling collapsing against body 107 after deployment. Delivery system 200 may then be moved to better align mobile external coupling with the branch artery, in this case, the brachiocephalic trunk 308. Further, due to the configuration of mobile external coupling 120, even if it is not perfectly aligned with brachiocephalic trunk 308, the top of the mobile external coupling 120 may move as it contacts and is being moved closers and closer and into the opening of the branch vessel to properly align it with brachiocephalic trunk 308 without having to move the entire stent-graft 100. As well, tension on branch guide wire 222 can be created by pulling either end of the wire. This tension will urge the distal end of the MEC distally away from the main graft and into the lumen of the branch vessel.

Figure 12:
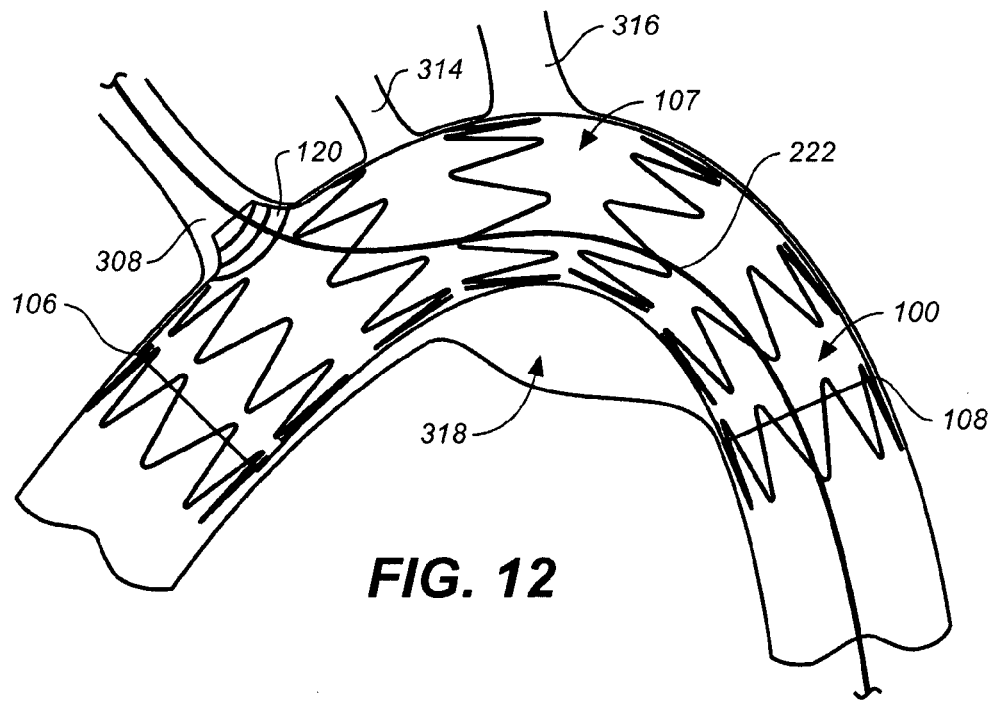
Figure 13:
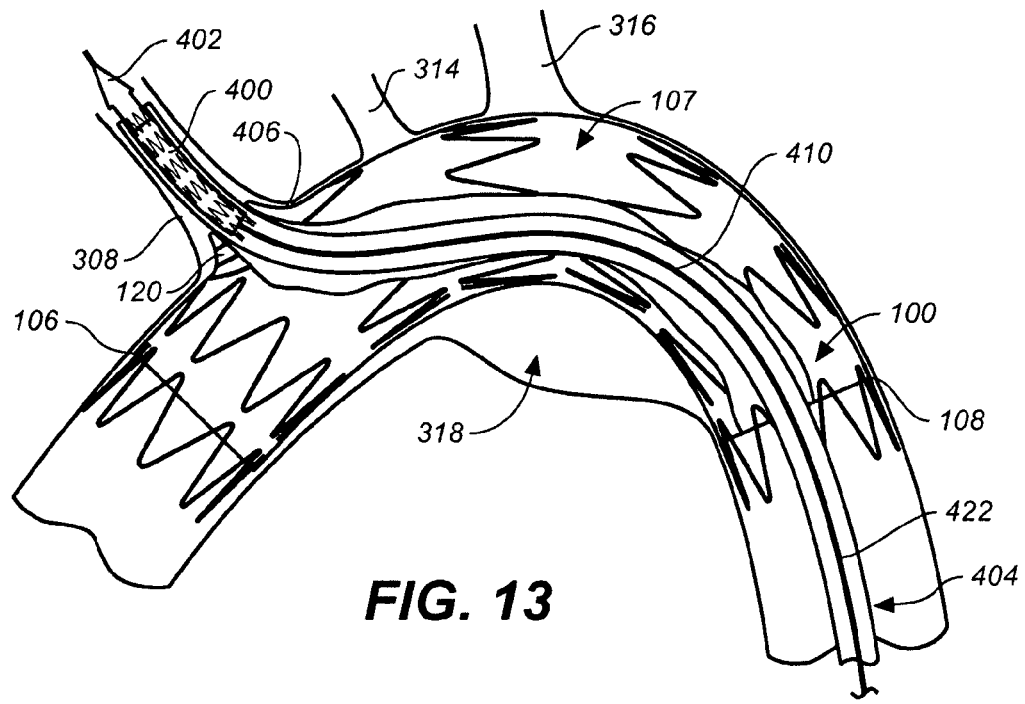
Figure 14:
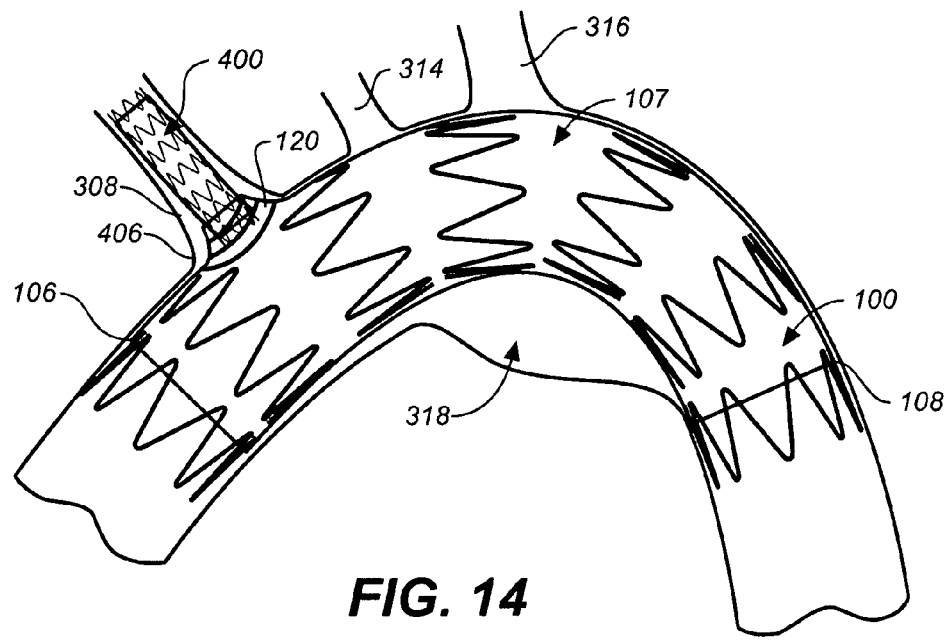

Once mobile external coupling 120 is deployed and in position in the brachiocephalic trunk 308, inner sleeve 214 may be retracted as explained above with respect to FIG. 8, thereby deploying the main body of the stent graft 100, as shown in FIG. 12. Once mobile external coupling 120 and stent-graft 100 are deployed, delivery system 200 may be removed. Second guidewire 222 may remain in place in brachiocephalic trunk 308 or may be replaced by another guidewire. A branch stent-graft delivery system 404 is advanced over second guidewire 222 and into brachiocephalic trunk 308, as shown in FIG. 13. Branch stent-graft delivery system includes a tip 402 and a sleeve (not shown), and contains therein a branch stent-graft 400. Branch stent-graft delivery system 404 and branch stent-graft 400 may be conventional. Branch stent-graft delivery system 404 is advanced into brachiocephalic trunk 308 such that a proximal portion 406 of branch stent-graft 400 remains inside of mobile external coupling 120. The sleeve constraining branch stent-graft 400 is then retracted proximally, thereby releasing branch stent-graft 400 from delivery system 404. The delivery system 404 is then withdrawn, as shown in FIG. 14. Because proximal portion 406 of branch stent-graft 400 is disposed within mobile external coupling 120 when branch stent-graft 400 is expanded, proximal portion 406 neck (narrows) at the top 126 of mobile external coupling 120 to conform with an inside surface of mobile external coupling 120.

Figure 15:
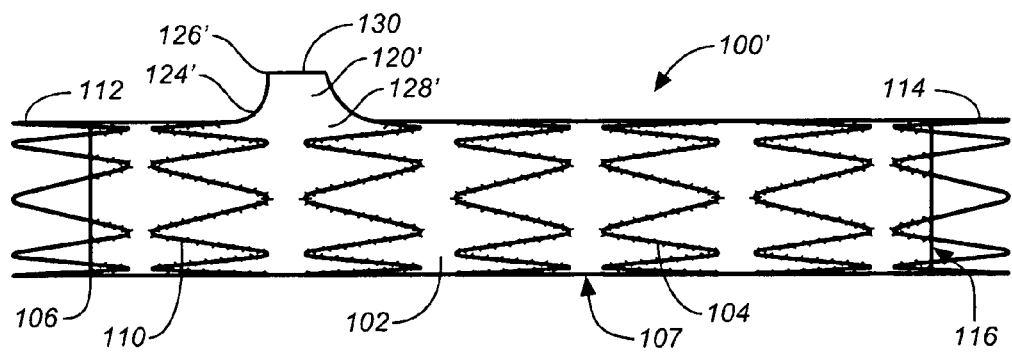
FIG. 15 is a schematic side view of a stent-graft in accordance with another embodiment hereof.

FIG. 15 shows an alternative embodiment of a stent-graft 100'. Stent graft 100' is similar to stent-graft 100 shown in FIG. 1 and the same reference numerals have been used to identify the same parts. However, mobile external coupling 120' shown in FIG. 15 does not include a helical stent disposed therein. Mobile external coupling 120' includes a graft material 128', a base 124' coupled to body 107, and a top 126'. Top 126' includes a stent ring (not shown but similar to top 126 of helical stent 122 shown in FIG. 3). Mobile external coupling 120' is generally frustoconically shaped, although base 124' may be generally elliptical as described above with respect to mobile external coupling 120. The dimensions described above with respect to stent-graft 100 are similarly applicable to stent-graft 100' and the delivery system and method described above may be similarly used with respect to stent-graft 100'.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. It will also be understood that each feature of each embodiment discussed herein, and of each reference cited herein, can be used in combination with the features of any other embodiment. All patents and publications discussed herein are incorporated by reference herein in their entirety.

What is claimed is:

1. An endovascular prosthesis comprising:
   a tubular body having a proximal end, a distal end, and a body lumen disposed between the proximal and distal ends, the tubular body including a body graft material and a plurality of stents coupled to the body graft material; and
   a mobile external coupling integral with the tubular body and including an extended configuration wherein the mobile external coupling extends outwardly from a side surface of the tubular body wherein the mobile external coupling is generally frustoconically shaped and includes a base coupled to the tubular body, a top spaced from the tubular body, and a coupling lumen disposed between the base and the top, wherein the coupling lumen is in flow communication with the body lumen and wherein the mobile external coupling includes a coupling graft material; and
   a helically shaped stent coupled to the coupling graft material, wherein the mobile external coupling and the stent include a compressed configuration wherein the mobile external coupling and the stent are collapsed against an outside surface of the tubular body such that the mobile external coupling is disposed outside of the body lumen in the compressed configuration, and wherein the stent is configured to provide an outward force away from the tubular body such that the mobile external coupling pops out from the tubular body when released from a restraining force.

2. The prosthesis of claim 1, wherein the coupling graft material is an extension of the body graft material.

3. The prosthesis of claim 1, wherein the coupling graft is attached to the body graft material with sutures.

4. The prosthesis of claim 1, wherein the base is generally elliptical in shape and the top is generally circular in shape.

5. The prosthesis of claim 4, wherein the base includes a major axis that is in the range of 20-30 mm and a minor axis that is in the range of 15-20 mm.

6. The prosthesis of claim 1, wherein the top includes a diameter in the range of 6-9 mm.

7. The prosthesis of claim 1, wherein the helically shaped stent is formed from a shape memory material.

8. The prosthesis of claim 7, wherein the shape memory material is a nickel-titanium alloy.

9. A main prosthesis and a branch prosthesis assembly comprising:
   a main prosthesis configured for placement in a main vessel, the main prosthesis including a tubular body and a mobile external coupling, the tubular body having a proximal end, a distal end, a body lumen disposed between the proximal and distal ends, and a body graft material, the mobile external coupling extending outwardly from a side surface of the tubular body and integral with the tubular body, and the mobile external coupling including a generally frustoconically shaped coupling graft material with a helically shaped stent coupled to the coupling graft material and including a coupling lumen in flow communication with the body lumen, wherein the stent is configured to provide an outward force away from the tubular body such that the mobile external coupling pops out from the tubular body when released from a restraining force maintaining the tubular body and mobile external coupling in a radially compressed configuration with the mobile external coupling collapsed against an outside surface of the tubular body such that the mobile external coupling is disposed outside of the body lumen in the compressed configuration; and
   a branch prosthesis configured for placement in a branch vessel that extends from the main vessel, the branch prosthesis including an outer surface in contact with an inner surface of the mobile external coupling;
   wherein the mobile external coupling includes a base attached to the tubular body and a top spaced from the tubular body, and wherein a distal portion of the mobile external coupling overlaps with a proximal portion of the branch prosthesis.

10. The assembly of claim 9, wherein the base is generally elliptical in shape and the top is generally circular in shape.

11. The assembly of claim 10, wherein the base includes a major axis that is in the range of 20-30 mm and a minor axis that is in the range of 15-20 mm.

12. The assembly of claim 9, wherein the top includes a diameter in the range of 6-9 mm.

13. The assembly of claim 12, wherein the helically shaped stent is formed from a shape memory material.

14. The assembly of claim 13, wherein the shape memory material is a nickel-titanium alloy.

15. The prosthesis of claim 1, wherein the mobile external coupling has a height of 10 to 15 millimeters.

16. The prosthesis of claim 9, wherein the mobile external coupling has a height of 10 to 15 millimeters.

17. A method for excluding an aneurysm at a target location near a junction of a main vessel and a branch vessel, comprising the steps of:
   delivering a main prosthesis in a compressed configuration to the target location in the main vessel, wherein the main prosthesis includes a tubular body and a mobile external coupling integral with the tubular body, the tubular body having a proximal end, a distal end, a body lumen disposed between the proximal and distal ends, and a body graft material, wherein in the compressed configuration, the mobile external coupling is collapsed against an outside surface of the tubular body such that the mobile external coupling is disposed outside of the body lumen in the compressed configuration;
   retracting a sleeve to expose the mobile external coupling such that the mobile external coupling extends outwardly from the tubular body;
   aligning the mobile external coupling with the branch vessel; and
   deploying the tubular body such that the tubular body expands from the compressed configuration to an expanded configuration,
   wherein the tubular body is disposed in the main vessel and the mobile external coupling extends into the branch vessel, and wherein the mobile external coupling includes a generally frustoconically shaped coupling graft material, a helically shaped stent coupled to the coupling graft material such that the helically shaped stent provides an outward force to extend the mobile external coupling outwardly away from the tubular body, and a coupling lumen in flow communication with the body lumen.

18. The method of claim 17, further comprising the steps of:
   delivering a branch vessel prosthesis in a compressed configuration to the branch vessel; and
   deploying the branch vessel prosthesis such that the branch vessel prosthesis radially expands to an expanded configuration and an outside surface of a portion of the branch vessel prosthesis is in contact with an inner surface of a portion of the mobile external coupling.

19. The method of claim 17, wherein the mobile external coupling includes a base attached to the tubular body and a top spaced from the tubular body.

20. The method of claim 17, wherein the base is generally elliptical in shape and the top is generally circular in shape.

21. The method of claim 20, wherein the base includes a major axis that is in the range of 20-30 mm and a minor axis that is in the range of 15-20 mm.

22. The method of claim 20, wherein the top includes a diameter in the range of 8-12 mm.

23. The method of claim 17, wherein the helically shaped stent is formed from a shape memory material.

24. The method of claim 23, wherein the shape memory material is a nickel-titanium alloy.

25. The method of claim 17, wherein main vessel is the aortic arch.

* * * * *

UNITED STATES PATENT AND TRADEMARK OFFICE
CERTIFICATE OF CORRECTION

| | | |
|---|---|---|
| PATENT NO. | : 8,506,622 B2 | Page 1 of 1 |
| APPLICATION NO. | : 12/425628 | |
| DATED | : August 13, 2013 | |
| INVENTOR(S) | : Bruszewski et al. | |

It is certified that error appears in the above-identified patent and that said Letters Patent is hereby corrected as shown below:

Title page, item [57], In the Abstract, lines 3-4

"coupled thereto with a forms a lumen" should read -- coupled thereto which forms a lumen --

In the Claims

Column 10, Line 56, Claim 25, "...wherein main vessel." should read -- ...wherein the main vessel. --

Signed and Sealed this
Twenty-third Day of December, 2014

Michelle K. Lee
*Deputy Director of the United States Patent and Trademark Office*